(12) United States Patent
Watt et al.

(10) Patent No.: US 7,178,518 B2
(45) Date of Patent: Feb. 20, 2007

(54) SPACER DEVICE

(75) Inventors: Paul M Watt, Mt Claremont (AU); Christopher Neil Martin, Connolly (AU)

(73) Assignee: Infamed, Ltd., Crawley (AU)

( * ) Notice: Subject to any disclaimer, the term of this patent is extended or adjusted under 35 U.S.C. 154(b) by 285 days.

(21) Appl. No.: 10/472,602

(22) PCT Filed: Mar. 21, 2002

(86) PCT No.: PCT/AU02/00332

§ 371 (c)(1),
(2), (4) Date: Feb. 17, 2004

(87) PCT Pub. No.: WO02/074371

PCT Pub. Date: Sep. 26, 2002

(65) Prior Publication Data

US 2005/0081850 A1    Apr. 21, 2005

(30) Foreign Application Priority Data

Mar. 21, 2001   (AU) ..................... PR3877

(51) Int. Cl.
A61M 11/00 (2006.01)
A61M 15/00 (2006.01)

(52) U.S. Cl. .............. 128/200.23; 128/203.15

(58) Field of Classification Search ........... 128/200.14, 128/200.18, 200.22, 200.23, 203.15, 203.18, 128/203.19, 203.12
See application file for complete search history.

(56) References Cited

U.S. PATENT DOCUMENTS

| 4,470,412 A | | 9/1984 | Nowacki et al. | |
| 5,042,467 A | * | 8/1991 | Foley | 128/200.23 |
| 5,427,089 A | | 6/1995 | Kraemer | |
| 5,477,849 A | | 12/1995 | Fry | |
| 5,848,588 A | | 12/1998 | Foley et al. | |
| 6,202,643 B1 | * | 3/2001 | Sladek | 128/200.23 |
| 6,578,571 B1 | * | 6/2003 | Watt | 128/200.14 |

FOREIGN PATENT DOCUMENTS

WO    WO 99/53982    10/1999

* cited by examiner

Primary Examiner—Teena Mitchell
Assistant Examiner—Amadeus Lopez
(74) Attorney, Agent, or Firm—Knobbe, Martens, Olson & Bear LLP

(57) ABSTRACT

A spacer unit inlet member integrally constructed of rigid or non-flexible material and capable of selectively mounting about its opening any one of a plurality of metered dose inhaler (MDI) actuators having different outlet size or shape. The inlet member includes a channel providing an opening of the inlet member and being formed by a wall substantially parallel to its rotational axis A peripheral edge of the wall is shaped substantially as a truncated oval. The inlet member further includes a pair of opposing curved walls surrounding and substantially parallel to the rotational axis of the channel and having an outermost edge comprising a substantially oval shape, and a wall substantially perpendicular to the rotational axis of the channel and positioned between the walls of the channel and the opposing curved walls.

11 Claims, 7 Drawing Sheets

SPACER DEVICE

This Application is a National Phase under 35 U.S.C. §371 of International Application PCT/AU02/00332, filed Mar. 21, 2002 designating the US and published in English as WO 02/074371, which claims the benefit of priority of Australian Provisional Application No. PR 3877, filed Mar. 21, 2001, both of which are incorporated herein by reference in their entireties.

FIELD OF THE INVENTION

The present invention relates generally to the field of medical devices for the inhalation of medicaments that comprise dry powder, liquid, or gas, and, more particularly to improvements to conventional spacer units designed for use with a metered dose inhaler (MDI), said improvement providing for the attachment of said spacer to a plurality of MDIs having differently shaped actuators.

All patents, patent applications, and publications cited herein are incorporated by reference in their entirety.

As used herein the words "from" or "of", and the term "derived from" shall be taken to indicate that a specified integer may be obtained from a particular source albeit not necessarily directly from that source.

As used herein, the term "substantially" shall be taken to mean that a stated integer approximates a stated characteristic, without a strict adherence to any mathematical formula or geometric consideration. For example, the term "substantially parallel" means that a stated integer approximates the parallel position or extends in the same direction as an integer with respect to which the reference is made, without being necessarily precisely parallel. Similarly, the term "substantially perpendicular" shall be taken to mean that a stated integer approximates the perpendicular position or extends in the transverse direction to an integer with respect to which the reference is made, without being necessarily precisely perpendicular.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Those skilled in the art will appreciate that the invention described herein is susceptible to variations and modifications other than those specifically described It is to be understood that the invention includes all such variations and modifications. The invention also includes all of the steps, features, compositions and compounds referred to or indicated in this specification, individually or collectively, and any and all combinations or any two or more of said steps, features, compositions and compounds.

The present invention is not to be limited in scope by the specific embodiments described herein, which are intended for the purposes of exemplification only. Functionally equivalent products, compositions and methods are clearly within the scope of the invention, as described herein.

BACKGROUND TO THE INVENTION

Inhalable medicaments, such as, for example, those for the prophylactic or therapeutic treatment of asthma or bronchitis, are commonly administered to patients using a metered dose inhaler (MDI). An MDI generally comprises a container housing the medicament, an axially extending vent tube from an internal valve, and a hollow actuator unit that houses the container and feeds the medicament to the patient via its outlet portion. The medicament is commonly packed in the container with a suitable propellant, such as, for example, a substance capable of forming a liquid under pressure and entering the gas phase at low pressure.

In use, the patient brings the outlet of the actuator to his/her mouth, depresses the container relative to the actuator, thereby activating the internal valve to dispense a measured dose of medicament into the patient's mouth. In this arrangement, it is often necessary for the patient to coordinate his/her inhalation with the depression of the container to ensure that a sufficient dose of the medicament enters the patient's airway. The medicament will generally include a liquid/gas mixture of propellant, wherein small drops of medicament/propellant mixture enter the patient's airway with the medicament and rapidly projected particles of medicament/propellant mixture are deposited in the throat and mouth and are swallowed. Accordingly, the need to coordinate the dispensing of medicament with the patient's inhalation, and the dispensing of medicament/propellant mixture from the MDI, reduce the efficiency of treatment. Moreover, there is a need to allow the deceleration and dispersal of particles to minimize deposition in the throat and mouth.

To enhance the efficacy of treatment, a spacer is commonly attached to the outlet of the actuator. Alternatively, the actuator is removed and the spacer is attached directly to the container via the vent tube. A spacer is a simple expansion chamber conveniently in the form of a small cylinder, conical or pear-shaped, into which a medicament that is dispensed from an MDI can be held prior to inhalation by a patient.

In use, one end of a spacer is attached to the outlet of the MDI, and the other end of the spacer is received into the patient's mouth. A sealing engagement between the spacer and the MDI is required to minimize drug/medicament leakage, thereby ensuring that an adequate dose of medicament is received by the spacer unit. The patient depresses the container of the MDI relative to the actuator, thereby activating the internal valve to dispense a measured dose of medicament into the spacer. In a separate action to dispensing of the medicament from the MDI, the patient inhales air/medicament/propellant mixture from the spacer into his/her airway. Accordingly, the spacer provides an advantage in so far as there is no need for the patient to coordinate his/her inhalation with the depression of the container of the MDI. Additionally, the spacer facilitates the deceleration and dispersal of particles of the medicament into smaller particles, for efficient inhalation.

As will be known to those skilled in the art, a rigid material, such as, for example, polycarbonate, is preferred for construction of a spacer. This is because such a rigid material confers strength and durability on the device. Additionally, polycarbonate is heat-resistant, facilitating steam sterilization and washing of the device in a dishwasher.

Standard spacers are constructed with at least two separate pieces: (i) a hollow inlet member having an opening for attaching an MDI actuator to facilitate the flow of medicament from the MDI to the spacer unit, (ii) a hollow outlet member having an opening for attaching a mouthpiece or mask to facilitate delivery of the medicament to the patient, and often (iii) a separate barrel-shaped element between elements (i) and (ii). During assembly, the components are snap-locked; or screwed together in sealing engagement to form an interior space for holding the medicament during use, and two openings to facilitate the flow of a medicament through the assembled unit.

Spacer devices are described in detail by Nowacki et al. in U.S. Pat. No. 4,470,412; and by InfaMed Limited in international Application No. PCT/AU99/00290.

Notwithstanding the advantages of using a spacer, such devices do increase the costs associated with treatment relative to the cost of the MDI alone. Moreover, as drug companies generally provide their MDI with an actuator having an outlet of a particular shape, not all actuator outlets are capable of being in sealing engagement with all spacer units. Accordingly, it is highly desirable for a spacer unit to be universally adaptable to all MDI devices.

One solution to this problem is to provide an "adaptor" or "back piece" that attaches to the end of the spacer and is capable of attaching to a plurality of actuator outlets. For example, the adaptor described in U.S. Pat. No. 5,848,588 (Trudell Medical International) comprises resilient, flexible material such as a rubber or the like, wherein concentric cylinders cover and grip the end of a cylindrical spacer, and a transverse membrane extends inwardly therefrom and is provided with a central opening, and straight and inwardly-directed ribs for receiving and gripping the outlet of the MDI. Pairs of the ribs have cross bracing, to control stretching of the diaphragm so that it provides a proper seal with an inserted MDI, whilst the radial inner ends of the ribs provide support for the MDI.

Spacer devices that do not require a separate adaptor have been designed to fit most known MDI units, with varying success. Generally, the provision of a universally-adaptable spacer of rigid construction has been avoided because such a device would have been prone to breaking and/or cracking, during fitting to MDI outlets of different shapes.

Occasionally, rigid spacer devices have been designed with prong-shaped protrusions to maximize flexure of the spacer to accommodate an MDI actuator. These protrusions are inherently brittle when made of a rigid plastic and are adaptable to very few types of actuators.

Accordingly, known spacers that are usable with a plurality of MDI devices generally require prior removal of the MDI container from the manufacturer's actuator, and subsequent fitting of the container to the spacer unit. Poor sealing between the vent tube of the MDI and the spacer may result during such procedures.

Alternatively, it is known to fit the spacer with a flexible inlet to accommodate various shaped MDI actuators. In fact, most conventional spacers that fit a plurality of different MDI actuators provide a flexible adaptor end that stretches or is compressed relative to the actuator. However, such an arrangement cannot be easily produced as an integral unit, because the spacer is generally made from rigid material, such as, for example, polycarbonate. This is a considerable disadvantage in terms of production of the device, because of the additional costs associated with producing separate pieces. Additionally, by providing a spacer in multiple pieces, with an additional rubber-like adaptor end piece, assembly of the device is made more complex, and requires additional effort either by the production team or the end user.

SUMMARY OF THE INVENTION

In work leading up to the present invention, the inventors sought to produce a cost-effective spacer unit that is capable of fitting a plurality of differently shaped MDI devices without the need for prior removal of the MDI canister from the actuator. The inventors realized that this object of the invention could be achieved by providing a spacer comprising a rigid material, such as that used in the manufacture of a conventional spacer device. To facilitate a reduction in production costs and time, the inventors produced such a spacer unit in as few as two separate pieces, each of said pieces being of an integral construction that could be produced, for example, from a single injection mold or by blow molding.

Accordingly, one aspect of the present invention provides a spacer unit inlet member integrally constructed of rigid or non-flexible material, said member capable of selectively mounting about its opening any one of a plurality of metered dose inhaler (MDI) actuators having different outlet size or shape, and comprising:

(i) a channel having a wall substantially parallel to its rotational axis and surrounding or substantially coaxial to the opening of said inlet member, wherein the peripheral edge of said channel is shaped substantially as a truncated oval having a major axis and having a pair of curved sides and a pair of opposite ends directed chordally of said oval and substantially perpendicular to the major axis of said oval;

(ii) a pair of opposing curved walls surrounding and substantially parallel to the rotational axis of said channel, and having an outermost edge comprising a substantially oval shape; and (iii) a wall substantially perpendicular to the rotational axis of said channel and positioned between said walls of said channel and said opposing curved walls.

In use, one or more of the external faces of said channel is/are capable of contacting the inner or outer wall of the outlet of an MDI actuator. Alternatively, or in addition, one or more of said opposing curved walls is/are capable of contacting the outer wall of the outlet of an MDI actuator. Alternatively, or in addition, the wall that is perpendicular to the rotational axis of the channel is also capable of contacting the peripheral edge of the outlet of an MDI actuator. The number and position of the contacts between the spacer inlet member and the MDI actuator outlet will depend upon the size and shape of the MDI actuator outlet, however al sealing engagement is formed between one or more faces of the MDI actuator outlet and one or more of said walls (i) or (ii) or (iii), to prevent the leakage of a medicament.

A second aspect of the present invention provides a spacer unit comprising:

(i) an inlet member integrally constructed of rigid or non-flexible material, said member capable of selectively mounting about its opening any one of a plurality of metered dose inhaler (MDI) actuators having different outlet size or shape, and including:

(a) a channel having a wall substantially parallel to its rotational axis and surrounding or substantially coaxial to the opening of said inlet member, wherein the peripheral edge of said channel is shaped substantially as a truncated oval having a major axis and having a pair of curved sides and a pair of opposite ends directed chordally of said oval and substantially perpendicular to the major axis of said oval;

(b) a pair of opposing curved walls surrounding and substantially parallel to the rotational axis of said channel, and having an outermost edge comprising a substantially oval shape; and (c) a wall substantially perpendicular to the rotational axis of said channel and positioned between said walls of said channel and said opposing curved walls, and (ii) a spacer unit outlet member is provided, and wherein said inlet member and said outlet member are locked together in sealing engagement to form an interior space for holding a medicament during use, and two openings to facilitate the flow of a medicament through the assembled unit.

The invention will best be understood from the following description of preferred embodiments when taken in connection with the accompanying non-limiting drawings.

DETAILED DESCRIPTION OF THE PREFERRED EMBODIMENTS

Figure 1:
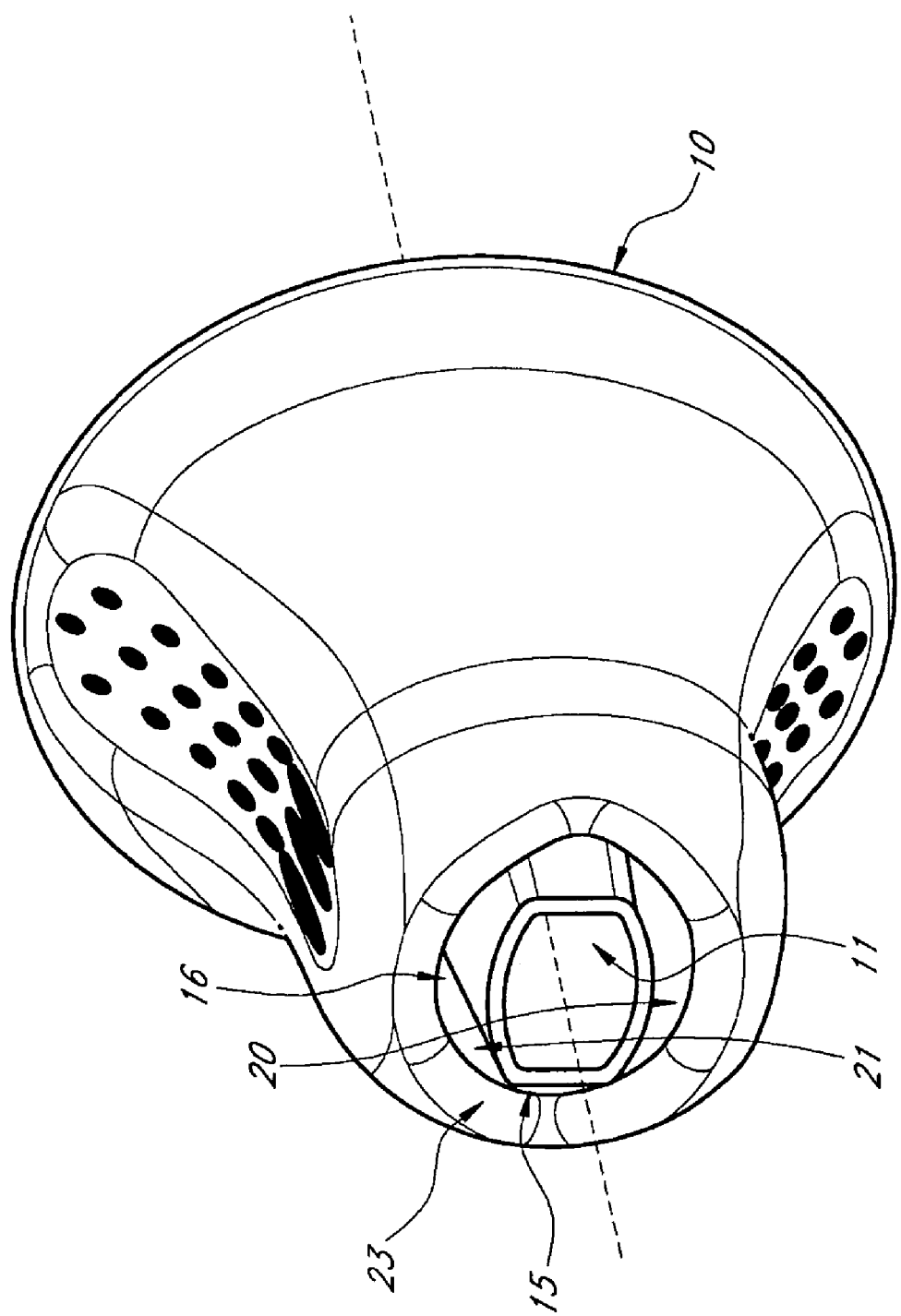
FIG. 1 is a perspective view of a spacer inlet member having one edge (10) for engaging a spacer outlet member (not shown) and an opposing opening (11) for attaching an MDI actuator (not shown) and through which a medicament is released into the assembled spacer device during use. The spacer inlet member is a hollow member having a rotational axis indicated by the broken line. Surrounding opening (11) is a channel (16) having a plurality of walls substantially parallel to the rotational axis of the inlet member, and a peripheral edge (15) shaped substantially as a truncated oval. The channel is surrounded by opposing curved walls (20 and 21) substantially parallel to the rotational axis of the channel, and having an outermost edge (23) substantially oval in shape with a major axis that is parallel to the major axis of the peripheral edge of the channel. The external face of the spacer inlet member has two opposing non-slip panels (stippled). Contour lines are also shown.

The term "spacer unit inlet member" includes that portion of a spacer unit that receives a medicament from an MDI or other drug deliver device. Similarly, the term "spacer unit outlet member" includes that portion of a spacer unit from which a medicament is directly or indirectly dispensed to a patient. It is preferable to construct a spacer device in separate portions, to facilitate cleaning of the device to remove excess medicament, either before changing the medicament to be administered, or in any event at regular intervals.

The spacer inlet member according to preferred embodiments of the invention may be constructed of any rigid or non-flexible material used to construct a standard spacer device. The terms "rigid" and "non flexible" includes having a flexibility less than a plastic that is normally used to construct an MDI actuator, and/or having a tensile strength greater than that of said plastic, including any non-rubberized material.

In this respect, the preferred embodiments of the present invention are predicated in part on the inventors' discovery that a range of different sized and different shaped MDI outlets can be stretched over a rigid spacer channel without leading to cracking or breaking of the spacer.

Preferred rigid or non-flexible materials for use in constructing the spacer inlet member of the present invention include polycarbonate, TPA, polypropylene, and polyvinylchloride. Mixed polymers, such as, for example, those comprising acrylonitrile, butadiene, and styrene (ABS polymer), are also contemplated. However, the use of polycarbonate is particularly preferred, because it is the material of choice for producing spacer devices, due to its clarity, strength, durability, and heat resistance properties.

The selective mounting feature of preferred embodiments of the present invention is provided by a specific modification to the opening end of a standard spacer inlet member. By "selective mounting" it is meant that any one of a number of different MDIs, such as, for example, the MDIs provided by Glaxo Smith Kline (e.g. Ventahaler™ MDI), 3M Corporation (e.g. the Autohaler™ MDI), AstraZeneca, or Rhône Poulenc Rorer (e.g. Azmacort™ MDI or Intal™ MDI), can be separately positioned in sealing engagement with the spacer inlet member, around its opening.

By "sealing engagement" is meant that two or more integers are in sufficient physical relation to prevent a degree of leakage of medicament that would compromise a dosage delivery to a patient. Persons skilled in the art will be aware of the leakage to be tolerated from an MDI without compromising its efficacy. Preferably, any such leakage is minimum and less than about 25% of the total dosage ejected from the MDI, more preferably less than about 5–10% of the total dosage.

As will be known to those skilled in the art, the term "opening" with reference to a spacer inlet member refers to that opening into which medicament is dispensed from an MDI during use. Those skilled in the art will also be aware that the opening of the spacer inlet member may be positioned anywhere on the surface of said inlet member, such as, for example, at an end opposing that end which engages the spacer outlet member, or alternatively, on any side surface of the spacer inlet member, without adversely affecting: the function of the assembled spacer unit.

Furthermore, preferred embodiments of the present invention are not limited by the overall size or shape of the spacer inlet member, the only requirement being that it is compatible with a spacer outlet member to which it is attached in use. For example, spacers of cylindrical shape, conical shape or pear shape are well known in the art, and the present invention encompasses spacer inlet members that are used for such spacers. Accordingly, the present invention is not to be limited to the frustoconical appearance of the spacer inlet member depicted in the accompanying drawings.

The surface of the spacer inlet member that interfaces with the MDI actuator outlet may be modified as desired. Persons skilled in the art will readily be capable of adapting the representation of the surface of the spacer inlet member that interfaces with an MDI actuator outlet, as depicted herein, to a variety of different shaped and sized spacer inlet members.

In this respect, it is known for conventional spacer devices to include a channel, such as, for example, a female or male fitting, surrounding the opening, or coaxial to the opening, wherein the MDI actuator outlet is generally attached in sealing engagement with said channel. Conventional channels will generally have one or more walls substantially parallel to the rotational axis of the channel, to direct the flow of medicament to the inside of the assembled spacer device.

In the present arrangement, the peripheral edge of the channel is shaped substantially as a truncated oval having a major axis and having a pair of curved sides and a pair of opposite ends directed chordally of said oval and substantially perpendicular to the major axis of said oval, to facilitate contact with a number of differently shaped MDI actuator outlets, either throughout its entire length, or at specific contact points.

For example, the MDI actuator outlet may perfectly match the: shape of the channel, and forms a sealing engagement with the complete internal face or complete external face of said channel.

Alternatively, the MDI actuator may not match the shape of the channel, or be too large to form a sealing engagement with the external face of the channel, in which case the MDI actuator outlet will either contact the channel at specific points along its external face, or not at all, and no sealing engagement will be formed that involves only the MDI actuator outlet and the channel. In such circumstances, the preferred embodiments of the present invention provide opposing walls that are curved and surround the channel, to hold the MDI in place. In this arrangement, one or more external faces of the channel and one or more internal faces of the surrounding opposing walls assist in holding, or actually hold, the actuator in place.

For example, the external face of the MDI actuator outlet may contact the surrounding opposing walls throughout its length, and form a sealing engagement therewith.

Alternatively, if the MDI actuator outlet does not match the shape of the surrounding opposing curved walls precisely, then the MDI may contact one or both of said walls at specific contact points.

Where such incomplete contact with the entire surface of the opposing curved walls does occur, the position of the MDI may be stabilized by further points of contact with a part of the external face of the channel, such as, for example, at the external face of one or more end walls of the channel, or at one or more corners of the channel, or at the external face of one or more of the curved walls of the channel.

It will be apparent from the preceding description that the nature of the contact between the MDI actuator outlet and the spacer inlet member will vary considerably between different MDI. The MDI actuator outlet can contact the spacer inlet member at one or more points, such as:
(i) the external face of the channel,
(ii) the internal face of the curved walls surrounding the channel;
(iii) the external walls running substantially perpendicular to the major axis of the peripheral edge of the channel, and four points on the internal face of the surrounding curved walls;
(iv) the external walls running substantially perpendicular to the major axis of the peripheral edge of the channel and the internal portions of the internal faces of the two opposing curved walls; and
(v) the external faces of the curved walls of the channel and one or more points on the internal faces of the surrounding opposing curved walls.

Where the above points of contact solus do not form a sealing engagement between the MDI actuator outlet and the spacer inlet member, then there is provided a third wall in the spacer inlet member of the invention, positioned between the channel and the opposing walls and substantially perpendicular thereto, that is capable of forming a sealing engagement with the peripheral edge of the actuator outlet, to prevent the leakage of medicament.

In use, the MDI actuator outlet may be compressed to fit within the outer opposing curved walls, or alternatively, stretched over the channel to form a sealing engagement with the spacer inlet member.

Accordingly, it will be apparent from the preceding description that the spacer inlet member performs both a holding and a sealing function.

Preferably, the spacer inlet member is provided with one or more internal one-way valves, filters or baffles, to permit the passage of medication in one direction only, generally within the opening. Such an arrangement is described in detail in International Application No. PCT/AU99/00290, which is incorporated herein by way of reference.

In a particularly preferred embodiment of the invention, the spacer inlet member has a configuration substantially as set forth in FIGS. 1 to 6. It is to be understood however, that the specific configuration set forth in the accompanying drawings is for the purposes of exemplification only, and should not be taken as imposing any limitation on the invention.

Figure 2:
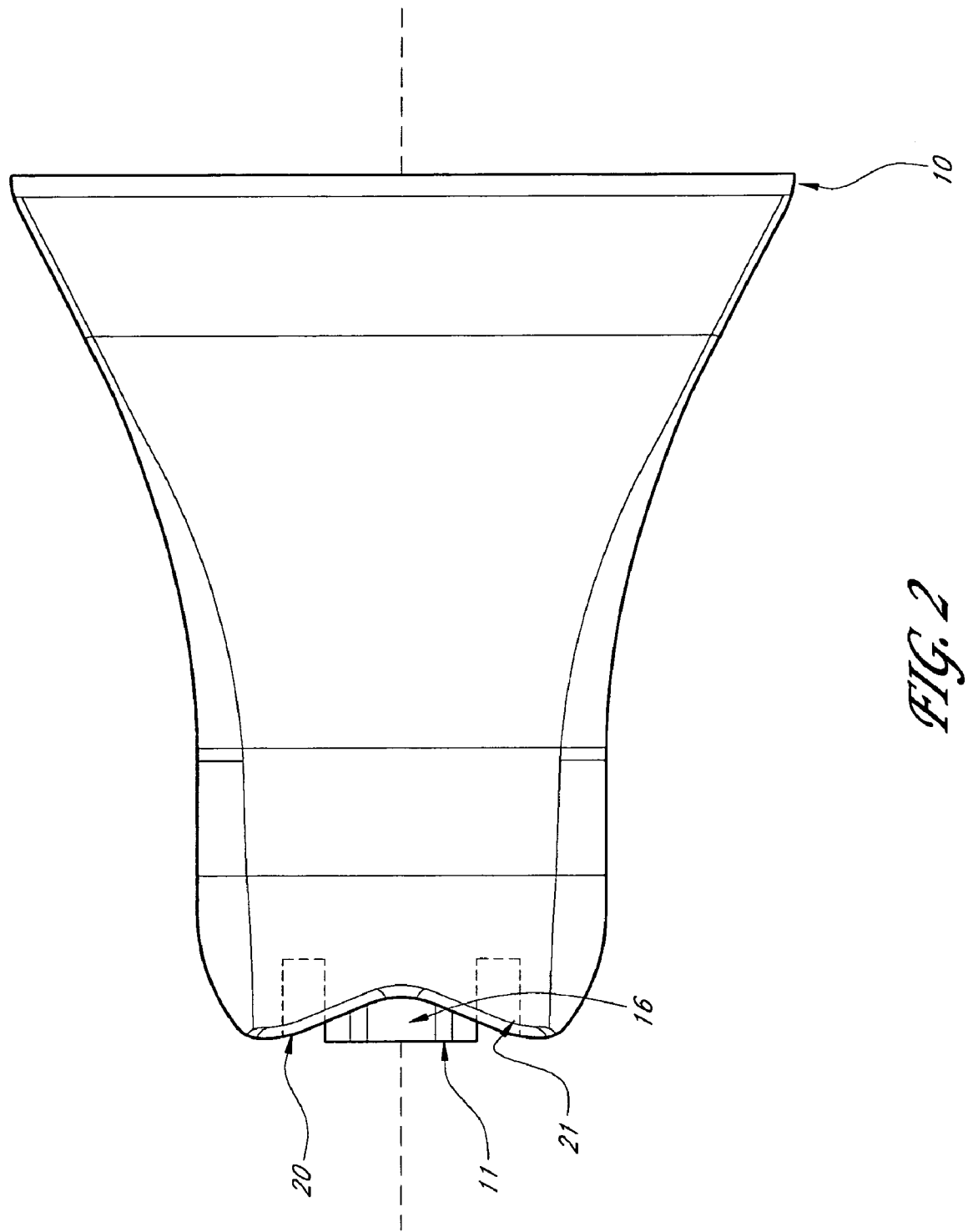
FIG. 2 is a lateral view of the spacer inlet member of FIG. 1 showing the edge (10) for engaging a spacer outlet member (not shown) and an opposing opening (11) for attaching an MDI actuator (not shown) and through which a medicament is released into the assembled spacer device during use. The position of the channel (16) is indicated, relative to the surrounding curved walls (20 and 21) that are contiguous with the external face of the spacer inlet member. The spacer inlet member has a rotational axis indicated by the broken line. Contour lines are also shown.

A spacer inlet member is depicted in FIGS. 1 and 2. The spacer inlet member comprises an integral, frustoconical body portion, having a rotational axis indicated by the broken line, and preferably constructed of clear polycarbonate. The body is hollow and open at both ends, and includes an opening or inlet end 11 shown at the left of FIGS. 1 and 2, and a second end 10, shown at the right of FIGS. 1 and 2, for forming a sealing engagement with a compatible spacer outlet member (not shown). The spacer inlet member is provided with grips on the external lateral surface to prevent or reduce slipping, and to assist the user to grip the assembled spacer unit. Surrounding opening (11) is a channel (16) having a plurality of walls substantially parallel to the rotational axis of the inlet member (broken line in FIGS. 1 and 2), and a peripheral edge (15) shaped substantially as a truncated oval. The peripheral edge 15 of channel 16 forms an edge of the spacer inlet member in the exemplified embodiment. However, it is possible to construct a spacer inlet member wherein the opening 11 is separated from the channel 16 and coaxial therewith, in which case the periphery of the spacer inlet member will form an opening that is not at the periphery of the channel. In use, medicament enters the spacer inlet member through opening 11. Surrounding channel 16 are two opposing curved walls 20 and 21, joined at their ends such that their outermost edge 23 forms an approximately oval shape. Edge 23 has a major axis that is parallel to the major axis of the peripheral edge of the channel in, the exemplified embodiment, however the present invention also encompasses alternative arrangements wherein these axes are perpendicular to each other. The opposing curved walls 20 and 21 that surround channel 16 are approximately parallel to the rotational axis of the spacer inlet member (broken line in FIGS. 1 and 2), and approximately parallel to the walls of channel 16. As shown in FIG. 2, it is not necessary for the walls 20 and 21 to be planar members. However, for most applications, the central portions of walls 20 and 21 are sufficiently prominent to be capable of forming a surface that contacts an MDI actuator outlet.

Figure 3:
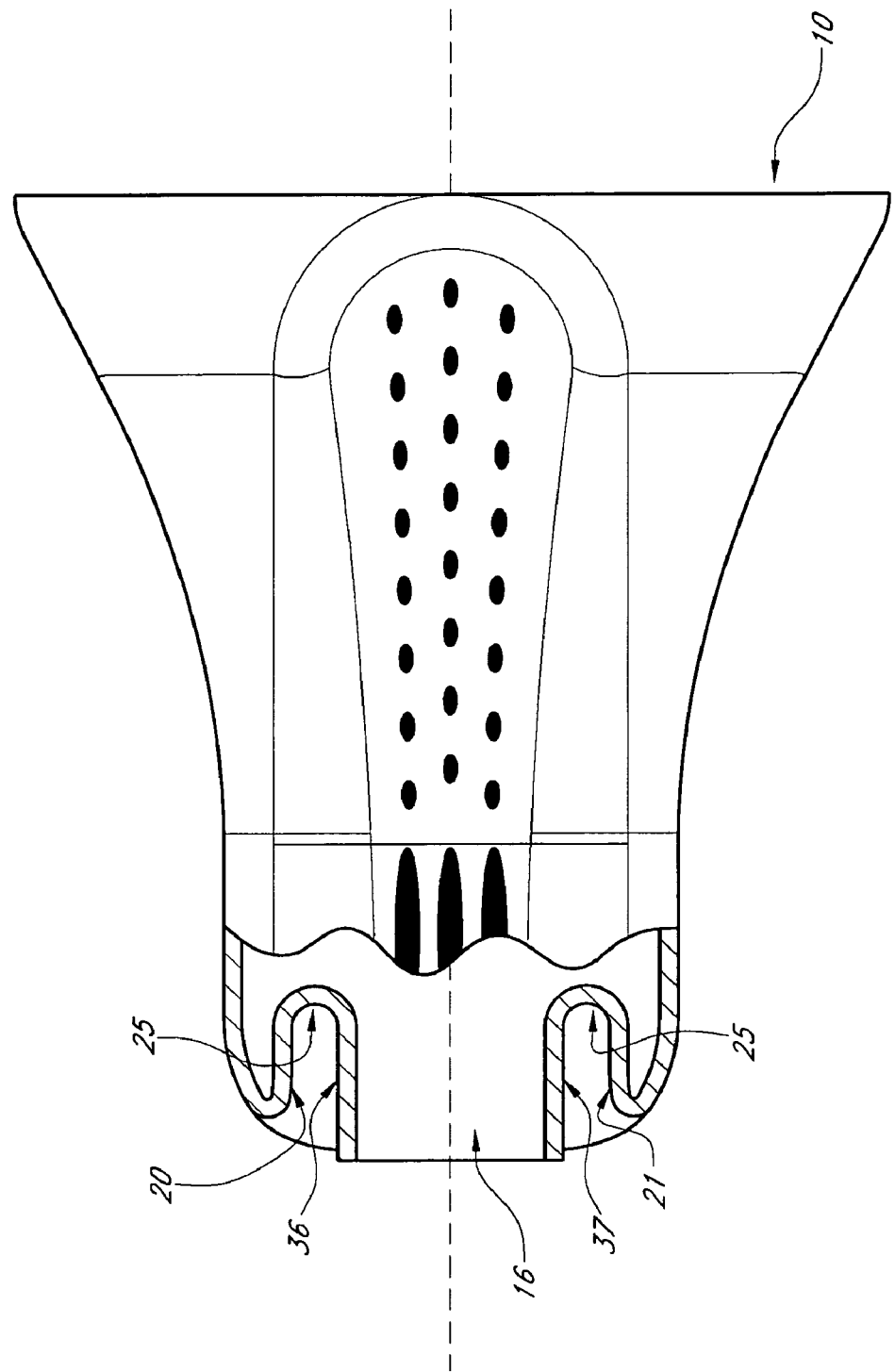
FIG. 3 is a top view of the spacer device of FIG. 1, with the portion of the end at which the MDI actuator is attached removed to reveal the holding faces and sealing faces of the spacer inlet member that attach the outlet of the MDI actuator during use. In particular, walls (36 and 37) of channel (16), and walls (20 and 21) form holding faces to position the outlet of the MDI actuator over the opening that surrounds channel (16). The peripheral; edge of the actuator forms a sealing engagement with the face (25) that consists in a surface between walls (36 and 37) and walls (20 and 21), said sealing face being substantially perpendicular to the rotational axis of channel (16). The edge (10) for engaging the spacer outlet member is also indicated. Broken line indicates the rotational axis of the channel Hatching indicates the contiguous external wall of the end portion of the spacer inlet member.
Figure 4:
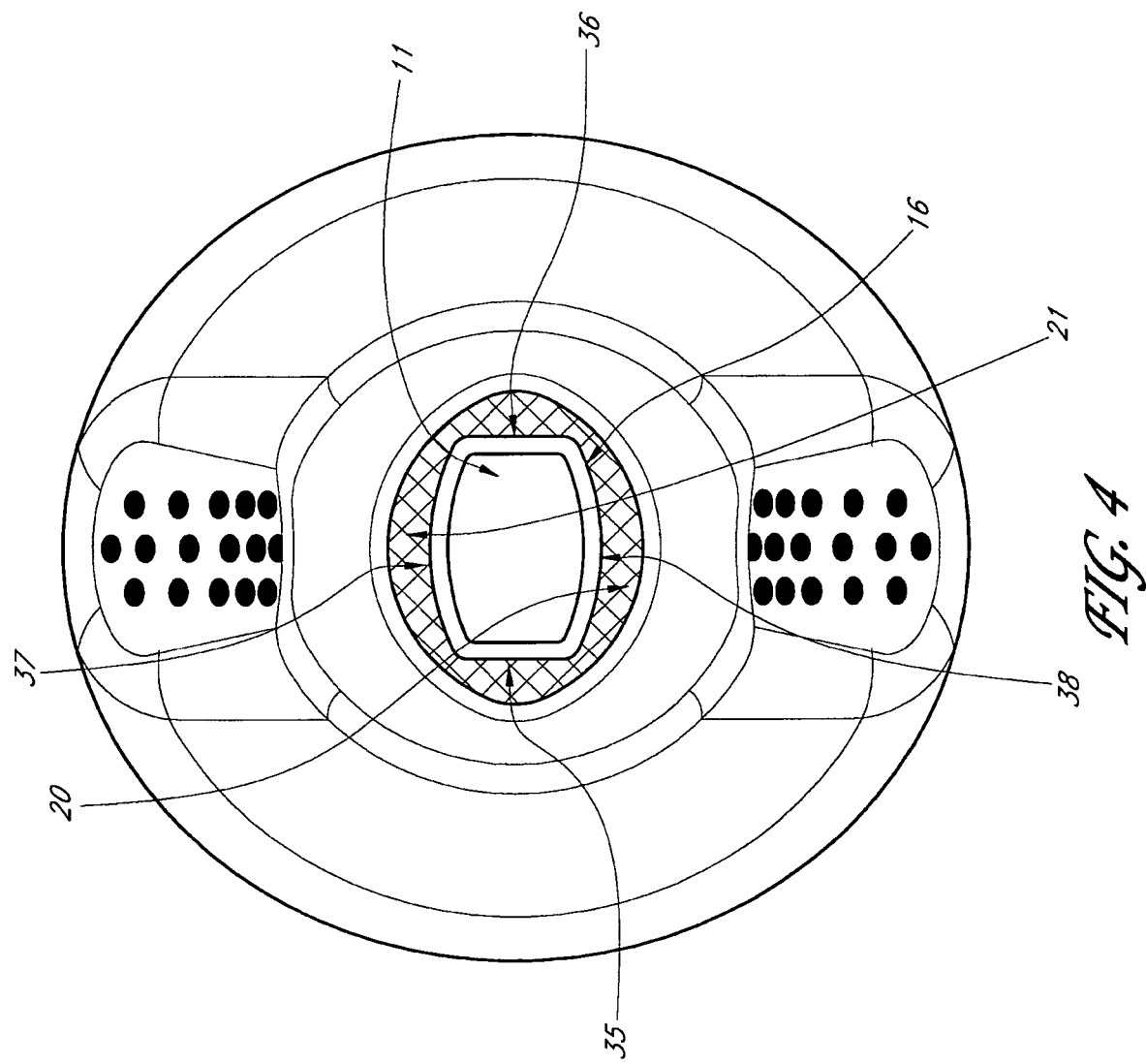
FIG. 4 is an end view of the spacer inlet member showing the relative positions of the opening (11), channel (16) and surrounding opposing walls (20 and 21). The external faces (35, 36, 37, and 38) of channel (16), and the internal faces of the opposing walls (20 and 21) are holding faces for positioning the outlet of the MDI actuator in place. A third face, indicated by the cross hatched area (integer 25 in FIG. 3), contacts the peripheral edge of the MDI actuator outlet.

The surfaces of the spacer inlet member that interface with the MDI actuator outlet are shown in greater detail in FIGS. 3 and 4. FIG. 3 shows two external faces 36 and 37, on the ends of channel 16 that are perpendicular to the major axis of its peripheral edge. External surfaces 36 and 37, as well as other external surfaces of channel 16 (e.g. surfaces 38 and 39 of FIG. 4), form holding surfaces that can contact the MDI actuator outlet in use. The internal surfaces of walls 20 and 21, that also form holding surfaces, are also shown in FIG. 3. A further wall 25 that is between and perpendicular to curved walls 20 and 21 and external walls 36 and 37, forms a third possible surface for contacting the MDI actuator outlet, as shown in FIGS. 3 and 4.

In use, and wherein the MDI actuator outlet has a shape substantially the same as that of the channel shown in FIG. 4, and is slightly larger in size than channel 16, the MDI actuator outlet will contact external faces 35, 36, 37, and 38 (FIG. 4) of channel 16, optionally extending throughout the length of channel 16 to also contact internal face 25, thereby forming a seal sufficient to minimize leakage of any dispensed medicament from said MDI. Some stretching of the MDI actuator outlet may be required to fit over the channel 16.

Alternatively, if the MDI actuator outlet has a rectangular or square shape, the MDI actuator outlet will contact external faces 35 and 36 of channel 16, and; four points on the internal face of the surrounding curved walls 20 and 21, optionally extending throughout the length of channel 16 to also contact internal face 25, thereby forming a seal sufficient to minimize leakage of any dispensed medicament from said MDI. Some compression or stretching of the MDI actuator outlet may be required to fit over the channel 16 and within the walls 20 and 21.

Alternatively, if the MDI actuator outlet has a shape that is the same as channel 16, but has different dimensions to channel 16, the MDI actuator outlet will contact external faces 35 and 36 of channel 16, and the central portions of the internal faces of walls 20 and 21, optionally extending throughout the length of channel 16 to also contact internal face 25, thereby forming a seal sufficient to minimize leakage of any dispensed medicament from said MDI. Some compression or stretching of the MDI actuator outlet may be required to fit over the channel 16 and within the walls 20 and 21.

Alternatively, wherein the MDI actuator has a shape substantially the same as the outer edge 23 (FIG. 1), the MDI actuator outlet will contact internal surfaces of walls 20 and 21 (FIG. 4), optionally extending throughout the length of walls 20 and 21 to also contact internal face 25, thereby forming a seal sufficient to minimize leakage of any dispensed medicament from said MDI. Some compression of the MDI actuator outlet may be required to fit within walls 20 and 21.

Alternatively, if the MDI actuator outlet is cylindrical or conical (i.e. having an approximately circular outer edge) it will contact the spacer inlet member at the four corners between external surfaces 35, 36, 37, and 38 of channel 16, and at an approximately central position of the inner surfaces of walls 20 and 21, optionally extending throughout the length of walls 20 and 21 to also contact internal face 25, thereby forming a seal sufficient to minimize leakage of any dispensed medicament from said MDI. Some compression of the MDI actuator outlet may to fit within walls 20 and 21, and/or stretching to fit over channel 16 may be required.

Preferably, the inlet member and the outlet member are snap-locked together, or alternatively, there are complementary threaded portions provided at the edges of the inlet and outlet members for screwing the parts together.

The spacer outlet member may be any conventional spacer outlet member, such as, for example, that described in International Application No. PCT/AU99/00290 or U.S. Pat. No. 4,470,412, amongst others. Preferably, the spacer outlet member is provided with one or more one way valves, filters or baffles, to confer a unidirectional flow of air and medicament from the assembled spacer device to the patient. Such a valve arrangement may be placed, for example, near the opening of the outlet member, and may include ducts to allow exhaled air/medicament mixture to be vented from the system into the surrounding atmosphere during exhalation. Such an arrangement is described in detail in international Application No. PCT/AU99/00290, which is incorporated herein by way of reference.

Preferably, the spacer unit includes a three way conduit or separator element to facilitate the attachment of one or more incentive toy units such as those described in International Application No. PCT/AU99/00290, to encourage infant users to use the spacer device, and teach a correct mode of breathing. According to this embodiment, the arrangement described in International Application No. PCT/AU99/00290 causes the inhaled medicament to be functionally separated from the toy units during the inhalation phase of breathing, to prevent the contamination of said toy units with medicament during use, thereby reducing the number of parts in need of regular cleaning.

Figure 5:
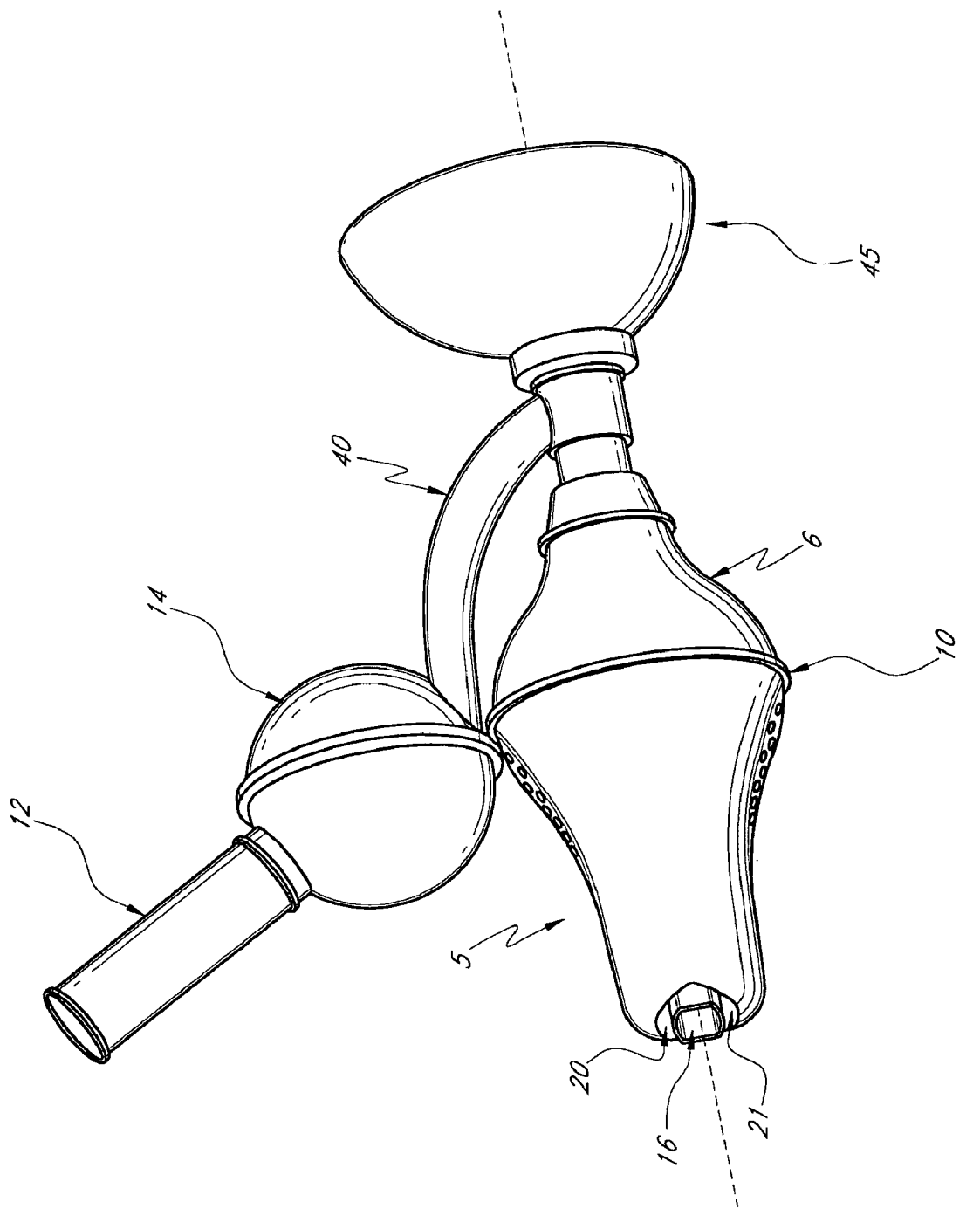
FIG. 5 is a perspective view of an assembled spacer unit comprising the spacer inlet member (5) as shown in FIGS. 1 to 4 in sealing engagement with a spacer outlet member (6) at outer edge (10) of said inlet member, and having a breath-activated incentive whistle (12) and a breath activated spinning orb (14) positioned between a mask (45) and spacer outlet member (6) via a three way conduit (40). The positions of the channel (16) and surrounding opposing walls (20 and 21) of the spacer inlet member are also indicated. The rotational axis of the spacer unit is indicated by the broken line.

A particularly preferred embodiment of the spacer device of the invention is shown in FIG. 5, wherein the spacer inlet member 5 is in sealing engagement with spacer outlet member 6, about edge 10 of the spacer inlet member. The positions of channel 16 and curved walls 20 and 21 of the spacer inlet member 5 are indicated, as is the rotational axis of the assembled spacer unit (broken line). A separator element, shown in FIG. 5 as a three way conduit 40, is attached at one end to the opening of spacer outlet member 6, at one end to a face mask 45, and at the other end to two toy units in series. The toy units are represented as a spinning orb 14 and a whistle 12. The facemask 45 could be readily substituted with a mouthpiece without compromising function. Wherein the assembled spacer unit has internal one way valves, these may be positioned within the spacer inlet member 5 and/or spacer outlet member 6, preferably near their openings. Alternatively, or in addition, such valves may be positioned at any end of the three way conduit 45 to facilitate the unidirectional flow of air or medicament over or through the toy units and/or through the assembled spacer device.

Figure 6:
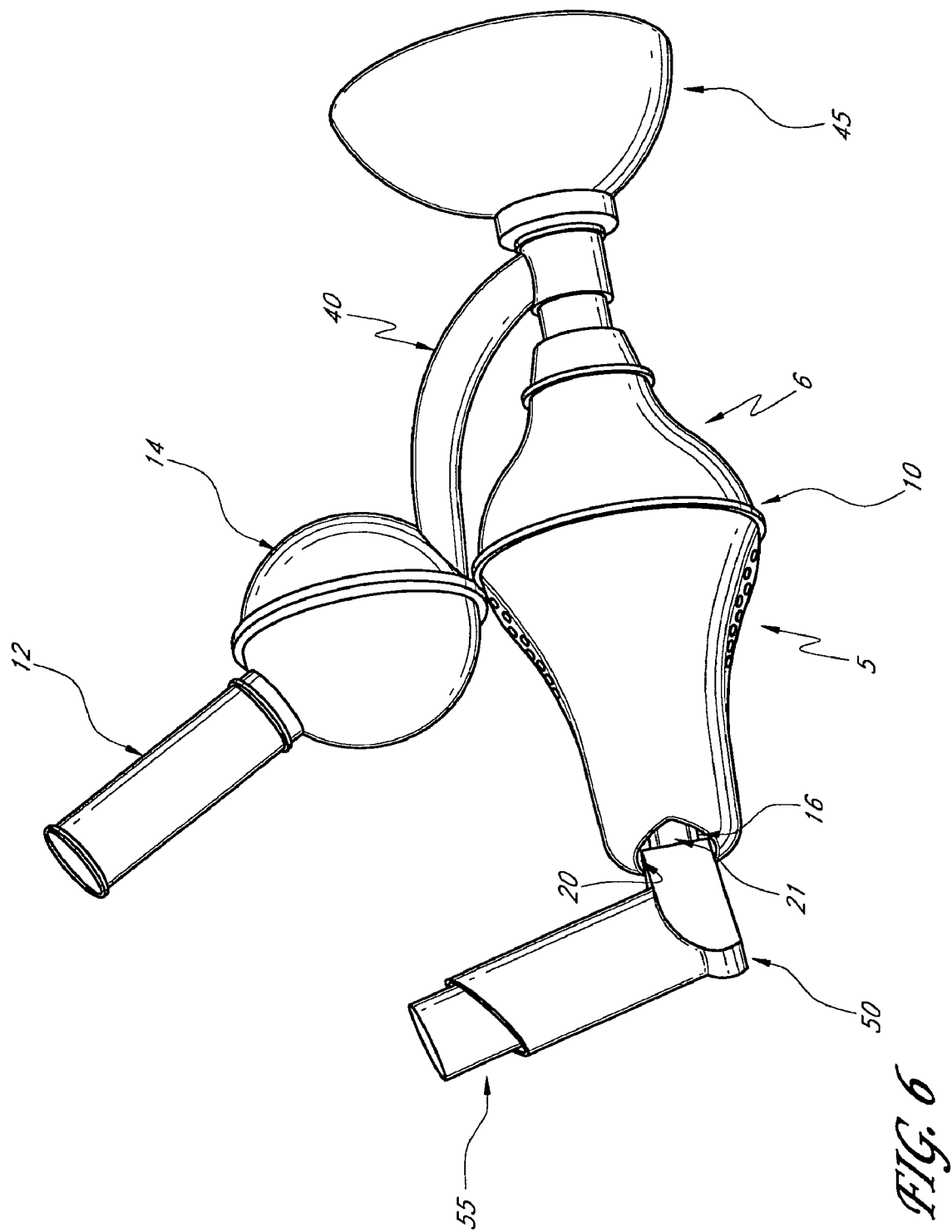
FIG. 6 is a perspective view showing the assembled spacer device of FIG. 5, with an MDI partially attached. The MDI comprises a canister or container (55) with medicament stored inside and an actuator (50). During assembly, the outlet of the actuator (50) is positioned around the channel (16), between the external walls of said channel and the surrounding opposing walls (20 and 21). For complete assembly, some stretching or compression of the actuator outlet may be required, before the actuator outlet is positioned with its peripheral edge in sealing engagement with the sealing face (not shown).

The MDI attaches to the assembled spacer device essentially as shown in FIG. 6, with the MDI actuator outlet 50 contacting the channel 16 and sliding between said channel and the surrounding curved walls 20 and 21. In use, medicament is released into the spacer device by depressing the canister 55 of the MDI relative to the actuator outlet 50.

Figure 7:
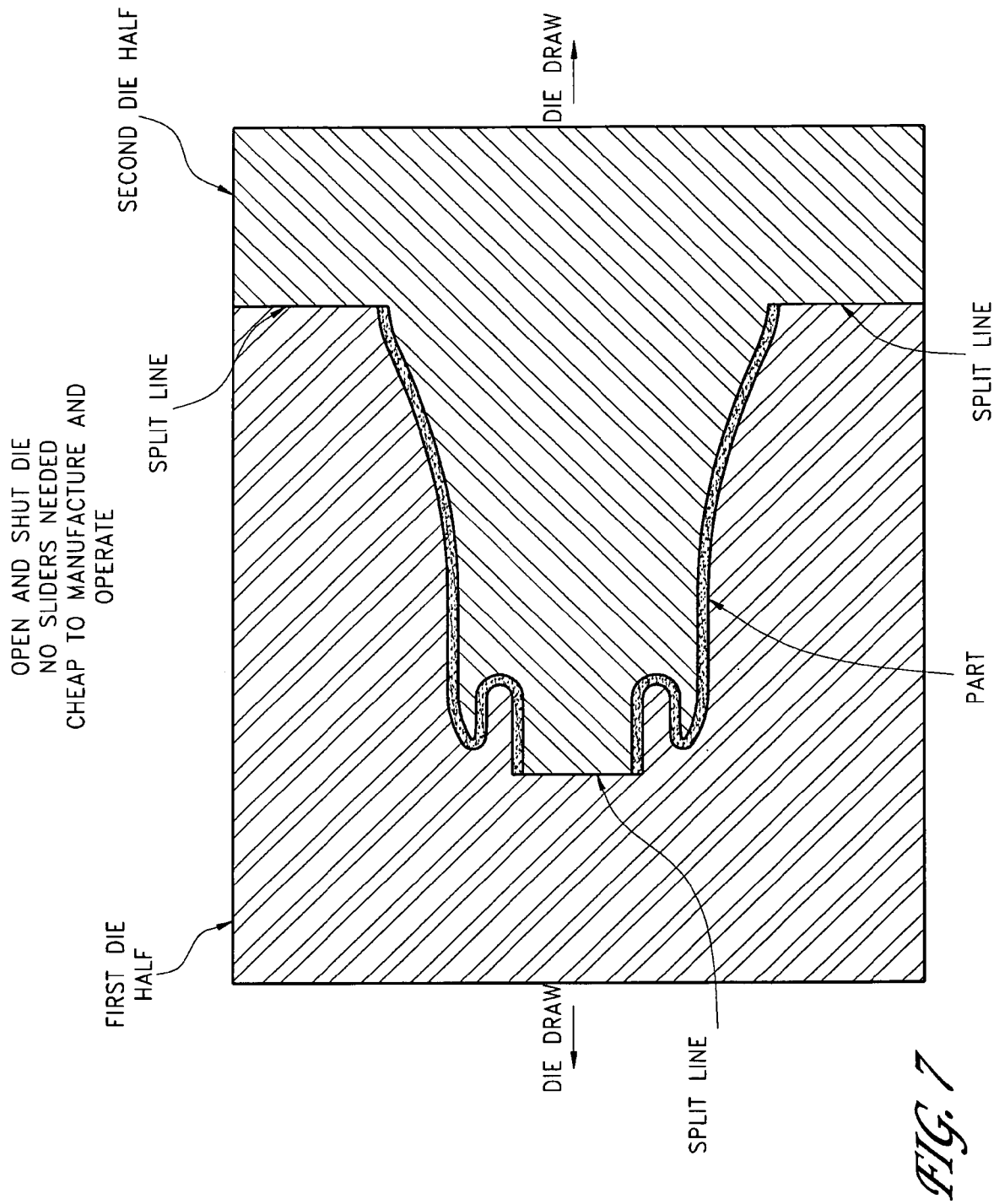
FIG. 7 is a sectional view of two halves (hatched areas) of an open and shut dye used to manufacture the spacer inlet member of FIG. 1 as an integral unit. The shaded line indicates the region of the dye to be occupied by the walls of the spacer inlet member during casting. Single unbroken lines indicate split lines separating the dye halves. The arrows indicate the direction of dye draw to separate the dye halves following casting.

An additional advantage of the spacer inlet member is that it can be produced inexpensively as an integral unit. For example, a single injection mold, such as using an 'open-and-shut' die that requires no sliding cores, and no undercuts, can be used to produce the inlet member. An example of such a die arrangement is shown in FIG. 7, wherein the body of the spacer inlet member is stamped or extruded between two dye halves, and then the dye halves are drawn apart, leaving the formed member as a hollow unit. In an alternative preferred embodiment, the invention can be produced by means of blow molding, a process known to those skilled in the art. Blow molding has the additional advantage of being less costly than other procedures for producing the improved spacer device of the invention.

The invention claimed is:

1. A spacer unit inlet member integrally constructed of rigid or non-flexible material, said member capable of selectively mounting about its opening a metered dose inhaler (MDI) actuator having an outlet of given size or shape, and comprising:
   (i) a channel providing an opening of said inlet member, said channel being formed by a wall substantially parallel to a rotational axis of said channel, wherein a peripheral edge of said wall is shaped substantially as a truncated oval having a pair of opposing curved sides and a pair of opposing chordal ends substantially perpendicular to a major axis of said peripheral edge,
   (ii) a pair of opposing curved walls substantially parallel to the rotational axis of said channel, and having an outermost edge comprising a substantially oval shape, and
   (iii) a wall substantially perpendicular to the rotational axis of said channel and positioned between said wall of said channel and said opposing curved walls.

2. The spacer unit inlet member according to claim 1, wherein one or more of external faces of said channel is/are capable of contacting an inner or outer wall of the outlet of the MDI actuator.

3. The spacer unit inlet member according to claim 1, wherein one or more of said opposing curved walls is/are capable of contacting an outer wall of the outlet of the MDI actuator.

4. The spacer unit inlet member according to claim 1, wherein the wall that is perpendicular to the rotational axis of the channel is also capable of contacting the peripheral edge of the outlet of the MDI actuator.

5. The spacer unit inlet member according to claim 1, wherein a sealing engagement is formed between one or more faces of the MDI actuator outlet and one or more of said walls (i) or (ii) or (iii), to prevent a leakage of a medicament.

6. A spacer unit comprising:
   (i) an inlet member integrally constructed of rigid or non-flexible material, said member capable of selectively mounting about its opening a metered dose inhaler (MDI) actuator having an outlet of given size or shape, and comprising:
      (a) a channel providing an opening of said inlet member, said channel being formed by a wall substantially parallel to a rotational axis of said channel wherein a peripheral edge of said wall is shaped substantially as a truncated oval having a pair of opposing curved sides and a pair of opposing chordal ends substantially perpendicular to a major axis of said peripheral edge;
      (b) a pair of opposing curved walls surrounding and substantially parallel to the rotational axis of said channel, and having an outermost edge comprising a substantially oval shape; and
      (c) a wall substantially perpendicular to the rotational axis of said channel and positioned between said wall of said channel and said opposing curved walls, and
   (ii) a spacer unit outlet member, and
   wherein said inlet member and said outlet member are locked together in sealing engagement to form an interior space for holding a medicament during use, and two openings to facilitate a flow of a medicament through the spacer unit.

7. The spacer unit according to claim 6, wherein the inlet member and the outlet member are snap-locked together.

8. The spacer unit according to claim 6, further comprising complimentary threaded portions provided at the edges of the inlet and outlet members for screwing the inlet and outlet members together.

9. The spacer unit according to claim 6, wherein the spacer outlet member further comprises one or more one way valves, filters or baffles, to confer a unidirectional flow of air and medicament from the spacer unit to a patient.

10. The spacer unit according to claim 6, wherein the spacer outlet member is integrally constructed of rigid or non-flexible material.

11. The spacer unit according claim 6, wherein the spacer unit further comprises a three way conduit or separator element to facilitate an attachment of one or more incentive toy units.

* * * * *